United States Patent
Terashima et al.

(10) Patent No.: US 11,089,977 B2
(45) Date of Patent: Aug. 17, 2021

(54) GAIT ANALYZING DEVICE, GAIT ANALYZING METHOD, AND COMPUTER-READABLE RECORDING MEDIUM

(71) Applicant: NEC Solution Innovators, Ltd., Tokyo (JP)

(72) Inventors: Hiroki Terashima, Tokyo (JP); Katsuyuki Nagai, Tokyo (JP); Tomomi Kinoshita, Tokyo (JP)

(73) Assignee: NEC Solution Innovators, Ltd., Tokyo (JP)

( * ) Notice: Subject to any disclaimer, the term of this patent is extended or adjusted under 35 U.S.C. 154(b) by 402 days.

(21) Appl. No.: 16/084,430

(22) PCT Filed: Mar. 30, 2017

(86) PCT No.: PCT/JP2017/013171
§ 371 (c)(1),
(2) Date: Sep. 12, 2018

(87) PCT Pub. No.: WO2017/170832
PCT Pub. Date: Oct. 5, 2017

(65) Prior Publication Data
US 2019/0076060 A1    Mar. 14, 2019

(30) Foreign Application Priority Data
Mar. 31, 2016    (JP) .............................. JP2016-072411

(51) Int. Cl.
*A61B 5/11*    (2006.01)
*G06T 7/20*    (2017.01)
(Continued)

(52) U.S. Cl.
CPC ................ *A61B 5/112* (2013.01); *A61B 5/00* (2013.01); *A61B 5/1128* (2013.01);
(Continued)

(58) Field of Classification Search
None
See application file for complete search history.

(56) References Cited

U.S. PATENT DOCUMENTS

2009/0076371 A1    3/2009    Lang et al.
2015/0324637 A1    11/2015    Utsunomiya et al.

FOREIGN PATENT DOCUMENTS

CN    101558996 A    10/2009
CN    104200200 A    12/2014
(Continued)

OTHER PUBLICATIONS

Office Action dated Jul. 3, 2020 in Chinese Application No. 201780017199.0.
(Continued)

*Primary Examiner* — Eric F Winakur
*Assistant Examiner* — Marjan Fardanesh
(74) *Attorney, Agent, or Firm* — Sughrue Mion, PLLC

(57) ABSTRACT

A gait analyzing device includes: a data acquisition unit acquiring first image data of a walking user and second image data of the walking user from a different direction, using a depth sensor; a skeletal information creation unit creating skeletal information identifying a position of a joint using depth information; a measurement information creation unit creating measurement information identifying a total number of steps and a ground contact history of left and right feet; a common part extraction unit comparing both instances of measurement information and extracts a part from the skeletal information in the first and second image data where the ground contact history is common; a correction processing unit correcting the skeletal information in the image data having the higher number of frames with the (Continued)

skeletal information in the image data having the lower number of frames; and an analysis processing unit analyzing the user's gait.

9 Claims, 13 Drawing Sheets

(51) Int. Cl.
*A61B 5/00* (2006.01)
*G16H 30/40* (2018.01)

(52) U.S. Cl.
CPC .............. *A61B 5/7221* (2013.01); *G06T 7/20* (2013.01); *A61B 5/1114* (2013.01); *A61B 5/4528* (2013.01); *A61B 5/4571* (2013.01); *A61B 5/4585* (2013.01); *G16H 30/40* (2018.01)

(56) References Cited

FOREIGN PATENT DOCUMENTS

| CN | 104463118 A | 3/2015 |
|---|---|---|
| JP | 2002-345783 A | 12/2002 |
| WO | 2007/131542 A1 | 11/2007 |
| WO | 2014/115817 A1 | 7/2014 |
| WO | 2016/031313 A1 | 3/2016 |

OTHER PUBLICATIONS

Naofumi Kitsunezaki et al., "KINECT applications for the physical rehabilitation", The Institute of Electronics, Information and Communication Engineers, IEICE Technical Report IE2012-89, Nov. 2012, pp. 41-46.

International Search Report for PCT/JP2017/013171, dated May 16, 2017.

Communication dated Oct. 23, 2019, from the European Patent Office in European Application No. 17775366.2.

Y.C. Chen et al., "Measurement of body joint angles for physical therapy based on mean shift tracking using two low cost Kinect images", 2015 37th Annual International Conference of the IEEE Engineering in Medicine and Biology Society (EMBC), IEEE, Aug. 25, 2015, pp. 703-706 (4 pages total).

Seongmin Baek et al., "Real-time performance capture using multiple Kinects", 2014 International Conference on Information and Communication Technology Convergence (ICTC), IEEE, Oct. 22, 2014, pp. 647-648 (2 pages total).

Yun Han et al., "Localization of RGB-D Camera Networks by Skeleton-based Viewpoint Invariance Transformation", 2013 IEEE International Conferences on Systems, Man, and Cybernetics, IEEE, Oct. 13, 2013, pp. 1525-1530 (6 pages total).

A. Elhayek et al., "Spatio-temporal Motion Tracking with Unsynchronized Cameras", 2012 IEEE Conference on Computer Vision and Pattern Recognition (CVPR), IEEE, Jun. 16, 2012, pp. 1870-1877 (8 pages total).

Fig.4

SKELETAL INFORMATION

| ELAPSED TIME | PELVIC AREA: X COORDINATE | PELVIC AREA: Y COORDINATE | PELVIC AREA: Z COORDINATE | CHEST/WAIST AREA: X COORDINATE | CHEST/WAIST AREA: Y COORDINATE | CHEST/WAIST AREA: Z COORDINATE | RIGHT THUMB: X COORDINATE | RIGHT THUMB: Y COORDINATE | RIGHT THUMB: Z COORDINATE | ...... |
|---|---|---|---|---|---|---|---|---|---|---|
| 0.56693 | 0.04 | −0.79 | 1.57 | 0.03 | −0.52 | 1.59 | 0.21 | −0.08 | 1.36 | |
| 0.59999 | 0.02 | −0.86 | 1.62 | 0.03 | −0.55 | 1.59 | 0.23 | −0.79 | 1.37 | |
| 0.63401 | 0.03 | −0.86 | 1.62 | 0.04 | −0.56 | 1.6 | 0.23 | −0.8 | 1.37 | |
| 0.66694 | 0.03 | −0.86 | 1.62 | 0.04 | −0.56 | 1.6 | 0.13 | −0.78 | 1.4 | |
| ...... | | | | | | | | | | |

Fig.7

MEASUREMENT INFORMATION

| ELAPSED TIME (SEC) | PITCH (SEC) | WALKING RHYTHM - RIGHT FOOT (SEC) | WALKING RHYTHM - LEFT FOOT (SEC) |
|---|---|---|---|
| 0 | 0 | 0 | 0 |
| 0.399985 | 0 | 0 | 0 |
| 0.766996 | 0.766996 | 0.766996 | 0 |
| 1.099990 | 0.766996 | 0.766996 | 0 |
| 1.434100 | 0.667107 | 0.766996 | 0.667107 |
| 1.734110 | 0.667107 | 0.766996 | 0.667107 |
| 2.066980 | 0.632881 | 0.632881 | 0.667107 |
| 2.399990 | 0.632881 | 0.632881 | 0.667107 |
| 2.534080 | 0.632881 | 0.632881 | 0.667107 |
| ..... | | | |

← FIRST STEP (row 3)
← SECOND STEP (row 5)
← THIRD STEP (row 7)

FIRST IMAGE DATA: TOTAL OF 10 FRAMES

SECOND IMAGE DATA: TOTAL OF 7 FRAMES

FIRST IMAGE DATA: TOTAL OF 18 FRAMES

SECOND IMAGE DATA: TOTAL OF 7 FRAMES

GAIT ANALYZING DEVICE, GAIT ANALYZING METHOD, AND COMPUTER-READABLE RECORDING MEDIUM

CROSS REFERENCE TO RELATED APPLICATIONS

This Application is a National Stage of International Application No. PCT/JP2017/013171 filed Mar. 30, 2017, claiming priority based on Japanese Patent Application No. 2016-072411 filed Mar. 31, 2016, the entire contents of which are hereby incorporated by reference.

TECHNICAL FIELD

The present invention relates to a gait analyzing device and a gait analyzing method for analyzing the walking motion of a person, and furthermore relates to a computer-readable recording medium in which is recorded a program for realizing the same.

BACKGROUND ART

Recent years have seen attempts to analyze the movement of humans using depth sensors such as Kinect (registered trademark). For example, Non Patent Document 1 discloses a system in which images of a rehabilitating patient moving his/her joints are captured using a depth sensor to measure the range of mobility of the patient's joints. It is conceivable that the system disclosed in Non Patent Document 1 could be used to analyze movement aside from that occurring during rehabilitation.

For example, the walking motion of a human can also be analyzed using the system disclosed in Non Patent Document 1. Falls while walking are highly likely to impact a person's health, leading to bedridden states and social withdrawal, particularly for the elderly. It is therefore important to predict the extent of a person's falling risk in advance. Analyzing walking motion using the system disclosed in Non Patent Document 1 can be considered useful in such predictions. In this case, it is sufficient for the subject of the analysis to simply walk toward the depth sensor.

LIST OF PRIOR ART DOCUMENTS

Non Patent Document

Non Patent Document 1: Kitsunezaki, N., Adachi, E., Yokota, T., and Mizusawa, J. "KINECT applications for the physical rehabilitation." The Institute of Electronics, Information and Communication Engineers, IEICE technical report IE2012-89; November 2012; p. 41-46.

DISCLOSURE OF THE INVENTION

Problems to be Solved by the Invention

Incidentally, with the system disclosed in Non Patent Document 1, the user to be analyzed must be located directly in front of the depth sensor in order to accurately analyze the movement. It is thus necessary for the user to walk toward the depth sensor when analyzing the user's walking motion.

However, when walking toward the depth sensor, the user may inadvertently mistake the depth sensor for an obstacle and suddenly reduce his/her walking speed or change his/her path near the depth sensor. In this case, there is a risk of reduced accuracy in the walking motion analysis.

One example of an object of the present invention is to provide a gait analyzing device, a gait analyzing method, and a computer-readable recording medium capable of solving the above problems and improving the accuracy of analysis when analyzing walking motion using a depth sensor.

Means for Solving the Problems

To achieve the above-described object, a gait analyzing device according to one aspect of the present invention includes:

a data acquisition unit that acquires, on a frame-by-frame basis, first image data obtained by using a depth sensor to capture an image of a walking user from a first direction angled relative to a travel direction and second image data obtained by using the depth sensor or a different depth sensor to capture an image of the walking user from a second direction angled, at a different direction from the first direction, relative to the travel direction;

a skeletal information creation unit that creates skeletal information identifying the position of a specific joint of the user, for all of the acquired image data, using depth information included in each of the first image data and the second image data;

a measurement information creation unit that creates measurement information identifying a total number of steps by the user and a ground contact history of the user's left and right feet, using all of the acquired image data, for each of the first image data and the second image data;

a common part extraction unit that compares the measurement information in all of the acquired first image data with the measurement information in all of the acquired second image data, and extracts, from the skeletal information in all of the acquired first image data and the skeletal information in all of the acquired second image data, a part where the ground contact history of the user's left and right feet is common;

a correction processing unit that, of the skeletal information in the extracted first image data and the skeletal information in the extracted second image data, corrects the skeletal information of the image data having the higher number of frames using the skeletal information of the image data having the lower number of frames; and an analysis processing unit that analyzes the user's gait using the corrected skeletal information.

Additionally, to achieve the above-described object, a gait analyzing method according to one aspect of the present invention includes:

(a) a step of acquiring, on a frame-by-frame basis, first image data obtained by using a depth sensor to capture an image of a walking user from a first direction angled relative to a travel direction and second image data obtained by using the depth sensor or a different depth sensor to capture an image of the walking user from a second direction angled, at a different direction from the first direction, relative to the travel direction;

(b) a step of creating skeletal information identifying the position of a specific joint of the user, for all of the acquired image data, using depth information included in each of the first image data and the second image data;

(c) a step of creating measurement information identifying a total number of steps by the user and a ground contact history of the user's left and right feet, using all of the acquired image data, for each of the first image data and the second image data;

(d) a step of comparing the measurement information in all of the acquired first image data with the measurement information in all of the acquired second image data, and extracting, from the skeletal information in all of the acquired first image data and the skeletal information in all of the acquired second image data, a part where the ground contact history of the user's left and right feet is common;

(e) a step of correcting, of the skeletal information in the extracted first image data and the skeletal information in the extracted second image data, the skeletal information of the image data having the higher number of frames using the skeletal information of the image data having the lower number of frames; and (f) a step of analyzing the user's gait using the corrected skeletal information.

Furthermore, to achieve the aforementioned object, a computer-readable recording medium according to one aspect of the present invention stores a program including commands that cause a computer to execute:

(a) a step of acquiring, on a frame-by-frame basis, first image data obtained by using a depth sensor to capture an image of a walking user from a first direction angled relative to a travel direction and second image data obtained by using the depth sensor or a different depth sensor to capture an image of the walking user from a second direction angled, at a different direction from the first direction, relative to the travel direction;

(b) a step of creating skeletal information identifying the position of a specific joint of the user, for all of the acquired image data, using depth information included in each of the first image data and the second image data;

(c) a step of creating measurement information identifying a total number of steps by the user and a ground contact history of the user's left and right feet, using all of the acquired image data, for each of the first image data and the second image data;

(d) a step of comparing the measurement information in all of the acquired first image data with the measurement information in all of the acquired second image data, and extracting, from the skeletal information in all of the acquired first image data and the skeletal information in all of the acquired second image data, a part where the ground contact history of the user's left and right feet is common;

(e) a step of correcting, of the skeletal information in the extracted first image data and the skeletal information in the extracted second image data, the skeletal information of the image data having the higher number of frames using the skeletal information of the image data having the lower number of frames; and (f) a step of analyzing the user's gait using the corrected skeletal information.

Advantageous Effects of the Invention

According to the present invention, the accuracy of analysis can be improved when analyzing walking motion using a depth sensor.

BRIEF DESCRIPTION OF THE DRAWINGS

FIGS. 3(a) to (c) illustrate different states.

FIG. 4 is a diagram illustrating an example of skeletal information created in the embodiment of the present invention.

FIG. 5(a) is for a horizontal direction of a screen and FIG. 5(b) is for a vertical direction of the screen.

FIG. 7 is a diagram illustrating an example of measurement information created in the embodiment of the present invention.

FIGS. 8(a) and (b) illustrate different examples.

FIG. 11(a) illustrates an example of skeletal information in first image data, FIG. 11(b) illustrates an example of skeletal information in second image data, and FIG. 11(c) illustrates an example of skeletal information after correction.

MODE FOR CARRYING OUT THE INVENTION

Embodiment

A gait analyzing device, a gait analyzing method, and a program according to an embodiment of the present invention will be described hereinafter with reference to FIGS. 1 to 13.

[Device Configuration]

Figure 1:
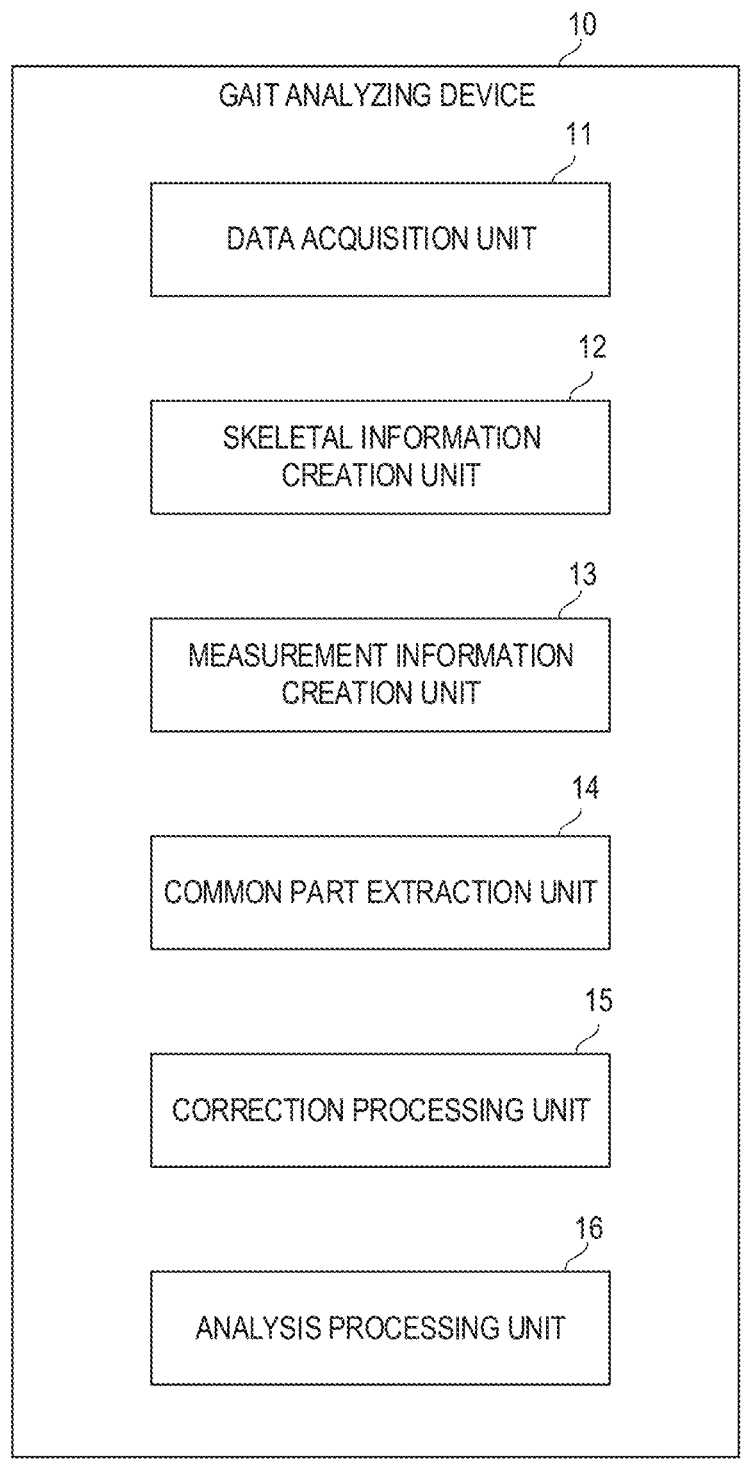
FIG. 1 is a block diagram illustrating the overall configuration of a gait analyzing device according to an embodiment of the present invention.

First, the overall configuration of the gait analyzing device according to the present embodiment will be described using FIG. 1. FIG. 1 is a block diagram illustrating the overall configuration of the gait analyzing device according to the embodiment of the present invention.

A gait analyzing device 10 according to the present embodiment, illustrated in FIG. 1, is a device for analyzing a user's gait. As illustrated in FIG. 1, the gait analyzing device 10 includes a data acquisition unit 11, a skeletal information creation unit 12, a measurement information creation unit 13, a common part extraction unit 14, a correction processing unit 15, and an analysis processing unit 16.

The data acquisition unit 11 acquires, on a frame-by-frame basis, first image data obtained by a depth sensor capturing images of a walking user from a first direction, which is at an angle relative to a travel direction. The data acquisition unit 11 also acquires, on a frame-by-frame basis, second image data obtained by the aforementioned depth sensor or a different depth sensor capturing images of a walking user from a second direction, which is at an angle, relative to the travel direction, is a direction different from the first direction.

The skeletal information creation unit 12 creates skeletal information identifying the positions of specific joints of the user, for all of the acquired image data, using depth information included in each of the first image data and the second image data.

The measurement information creation unit 13 creates measurement information identifying a total number of steps by the user and a ground contact history of the user's left and right feet, using all of the acquired image data, for each of the first image data and the second image data.

The common part extraction unit 14 compares the measurement information in all of the acquired first image data with the measurement information in all of the acquired second image data. The common part extraction unit 14 then extracts, from the skeletal information in all of the acquired first image data and the skeletal information in all of the acquired second image data, a part where the ground contact history of the user's left and right feet is common.

Of the extracted first image data and the extracted second image data, the correction processing unit 15 corrects the skeletal information of the image data having the higher number of frames using the skeletal information of the image data having the lower number of frames. The analysis processing unit 16 analyzes the user's gait using the corrected skeletal information.

Thus with the gait analyzing device 10, the user's gait can be analyzed using image data obtained in a state where the depth sensor is arranged in a position not directly in front of the user. This suppresses a situation in which the user inadvertently mistakes the depth sensor for an obstacle and suddenly reduces his/her walking speed or changes his/her path near the depth sensor. Thus according to the gait analyzing device 10, the accuracy of analysis can be improved when analyzing walking motion using a depth sensor.

Figure 2:
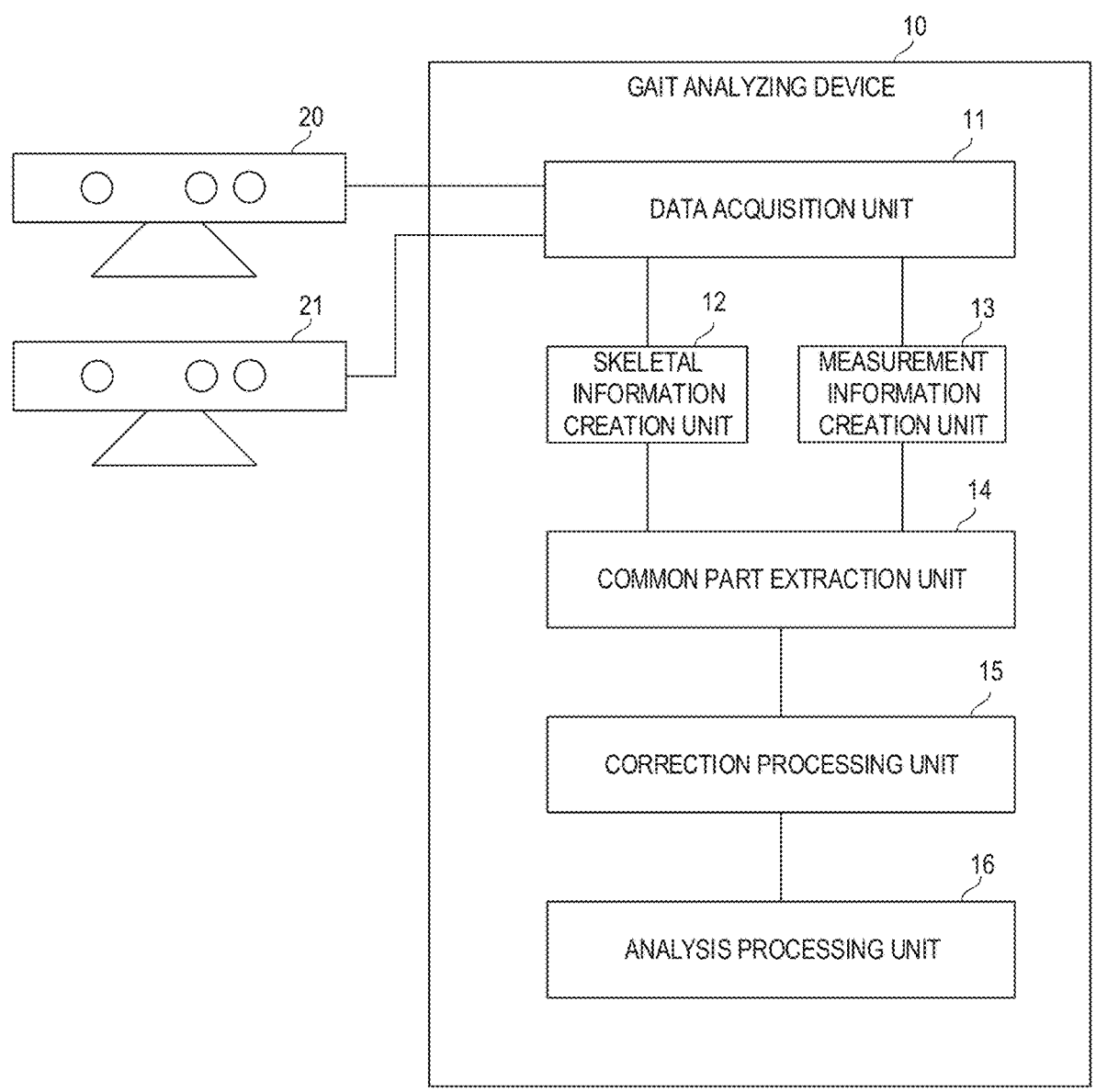
FIG. 2 is a block diagram illustrating the configuration of the gait analyzing device according to the embodiment of the present invention in more detail.

The configuration and functions of the gait analyzing device 10 according to the present embodiment will be described in detail next using FIGS. 2 to 11. FIG. 2 is a block diagram illustrating the configuration of the gait analyzing device according to the embodiment of the present invention in more detail.

As illustrated in FIG. 2, in the present embodiment, the gait analyzing device 10 is connected to depth sensors 20 and 21. The gait analyzing device 10 receives image data, in which a depth is added to each pixel, from the depth sensors 20 and 21 over wires or wirelessly. The depth sensors 20 and 21 include, for example, a light source that emits infrared laser light in a specific pattern and an image sensor that receives the infrared light after being reflected by an object, thereby outputting the image data to which a depth is added to each pixel. An existing depth sensor such as Kinect (registered trademark) can be given as a specific example of the depth sensors 20 and 21.

Figure 3A:
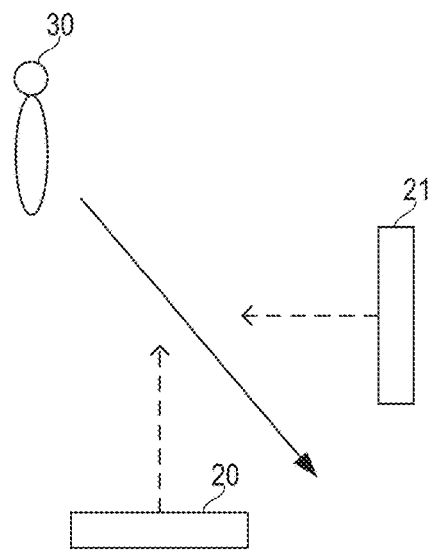
FIGS. 3(a)-3(c) are diagrams illustrating an example of the arrangement of depth sensors used in the present embodiment.
Figure 3B:
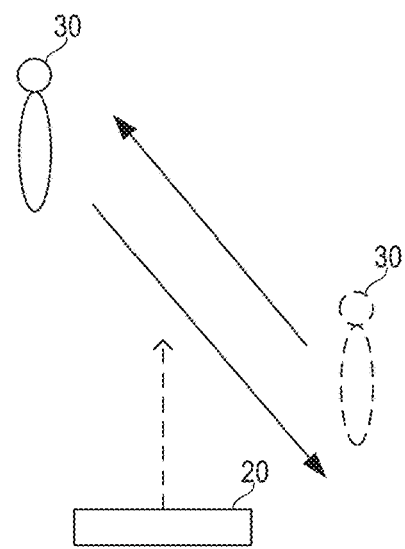
Figure 3C:
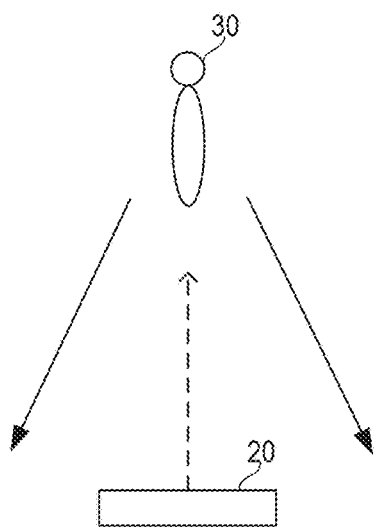

A relationship between the positions of the depth sensors and the travel direction of the user will be described here using FIGS. 3(a) to (c). FIGS. 3(a) to (c) are diagrams illustrating an example of the arrangement of the depth sensors used in the present embodiment. FIGS. 3(a) to (c) illustrate different states. In FIGS. 3(a) to (c), the solid line arrow represents the travel direction of a user 30, and the broken line arrows represent the image capturing directions of the depth sensors.

As illustrated in FIG. 3(a), in the present embodiment, the depth sensor 20 is arranged so as to capture an image of the walking user 30 mainly from the right side, whereas the depth sensor 21 is arranged so as to capture an image of the walking user 30 mainly from the left side. In other words, in the example illustrated in FIG. 3(a), the depth sensor 20 captures an image of the user 30 from a direction angled to the right relative to the travel direction of the walking user 30, whereas the depth sensor 21 captures an image of the user 30 from a direction angled to the left relative to the travel direction of the walking user 30.

However, in the present embodiment, only a single depth sensor may be arranged instead, as illustrated in FIGS. 3(b) and (c). For example, as illustrated in FIG. 3(b), if the user 30 walks so as to cross in front of the depth sensor 20, turns 180 degrees, and then returns, the single depth sensor 20 can capture an image of the walking user 30 from both a direction angled to the right and a direction angled to the left relative to the travel direction.

Furthermore, as illustrated in FIG. 3(c), if the user 30 has walked so as to exit the path of the depth sensor 20 to the left and furthermore walked so as to exit the path of the depth sensor 20 to the right, the single depth sensor 20 can capture an image of the walking user 30 from both a direction angled to the right and a direction angled to the left relative to the travel direction.

Assuming the depth sensors 20 and 21 are arranged as illustrated in FIG. 3(a), the data acquisition unit 11 acquires the first image data from the depth sensor 20 and acquires the second image data from the depth sensor 21. However, if only a single depth sensor is arranged in the manner illustrated in FIG. 3(b) or (c), the data acquisition unit 11 obtains the first image data and the second image data from the single depth sensor.

In the present embodiment, the skeletal information creation unit 12 calculates three-dimensional coordinates of specific joints of the user for each piece of image data, by using coordinates in the image data and the depths added to the pixels, and creates the skeletal information using the calculated three-dimensional coordinates. FIG. 4 is a diagram illustrating an example of the skeletal information created in the embodiment of the present invention. As illustrated in FIG. 4, the skeletal information is constituted by the three-dimensional coordinates of each of the joints, at each of elapsed times following the start of image capturing. In the present specification, an X coordinate is the value of a position in the image data with respect to the horizontal direction, a Y coordinate is the value of a position in the image data with respect to the vertical direction, and a Z coordinate is the value of the depth added to the pixel.

The head, the neck, the right shoulder, the right elbow, the right wrist, the right hand, the thumb of the right hand, the tip of the right hand, the left shoulder, the left elbow, the left wrist, the left hand, the thumb of the left hand, the tip of the left hand, the chest area, the chest/waist area, the pelvic area, the right hip joint, the right knee, the right ankle, the top of the right foot, the left hip joint, the left knee, the left ankle, the top of the left foot, and the like can be given as examples of specific joints. FIG. 4 illustrates an example of the three-dimensional coordinates for the pelvic area, the chest/waist area, and the right thumb (the thumb of the right hand).

Figure 5A:
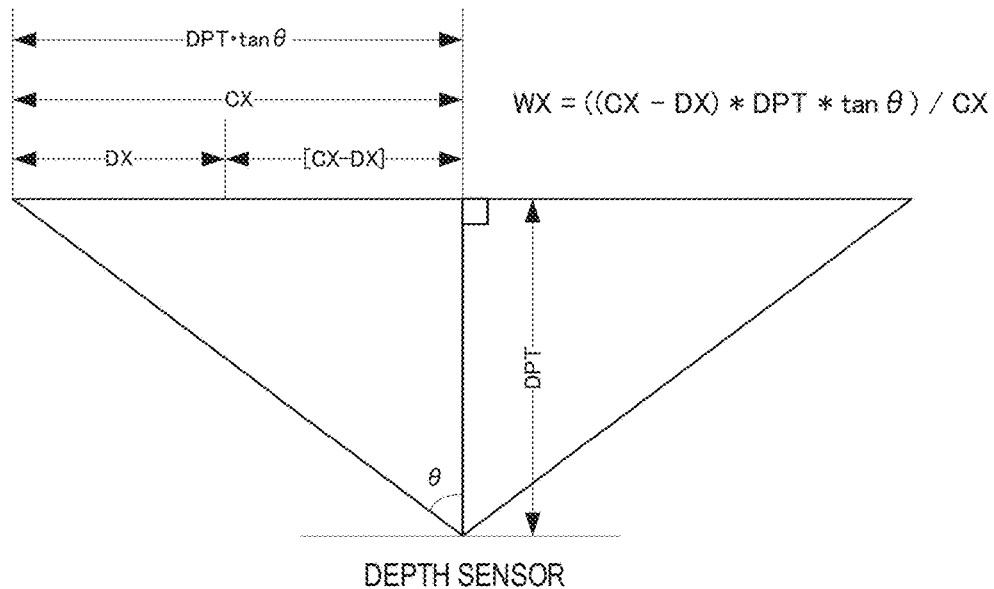
FIGS. 5(a) and 5(b) are diagrams illustrating a process of calculating three-dimensional coordinates according to the embodiment of the present invention, where
Figure 5B:
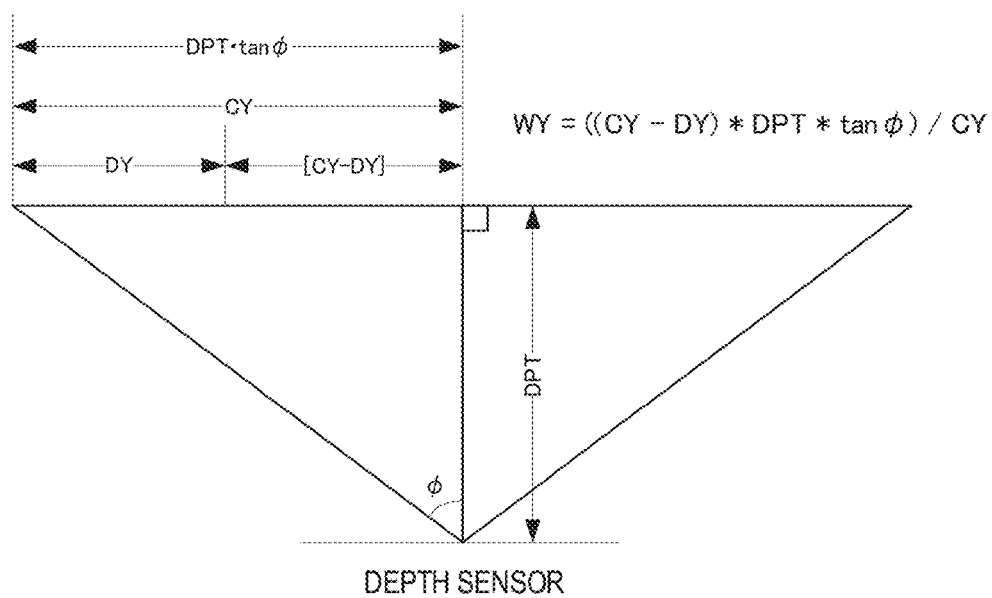

The method for calculating the three-dimensional coordinates from the coordinates and depth in the image data is as follows. FIGS. 5(a) and (b) are diagrams illustrating a process for calculating the three-dimensional coordinates according to the embodiment of the present invention, where FIG. 5(a) is for a calculation process for the horizontal direction of the image (the X coordinate) and FIG. 5(b) is for a calculation process for the vertical direction (the Y coordinate) of the image.

First, the coordinates of a specific point in the image data to which a depth has been added are represented by (DX, DY), and the depth at the specific point is represented by DPT. The number of pixels in the image data in the horizontal direction is represented by 2CX, and the number of pixels in the vertical direction is represented by 2CY. An angle of view of the depth sensor in the horizontal direction is represented by 2θ, and an angle of view in the vertical direction is represented by 2φ. In this case, three-dimensional coordinates (WX,WY,WZ) of the specific point can be calculated through the following Equations 1 to 3, as can be seen from FIGS. 5(a) and (b).

$$WX=((CX-DX) \times DPT \times \tan\theta)/CX \quad \text{[Equation 1]}$$

$$WY=((CY-DY) \times DPT \times \tan\varphi)/CY \quad \text{[Equation 2]}$$

$$WZ=DPT \quad \text{[Equation 3]}$$

In the present embodiment, the measurement information creation unit 13 first determines whether or not the user's foot is in contact with a ground surface, and then identifies the timing at which the foot contacts the ground surface, i.e., a ground contact timing, in each of the first image data and the second image data. The measurement information creation unit 13 then creates the measurement information from the identified ground contact timing.

Figure 6:
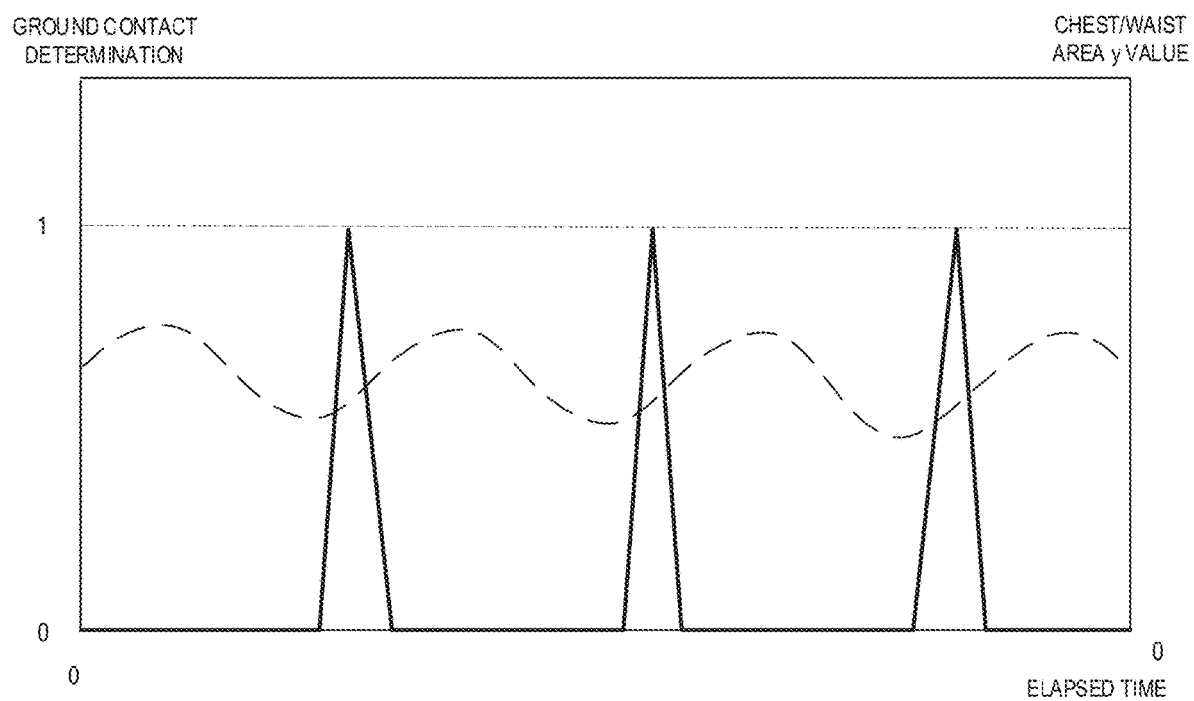
FIG. 6 is a diagram illustrating an example of changes over time in the value of a Y coordinate (y value) of the user's chest/waist area and a ground contact determination result.
Figure 8:
FIGS. 8(a) and (b) are diagrams illustrating an example of a supplementation process carried out in the embodiment of the present invention when numbers of frames do not match.
Figure 8:
Figure 8:
Figure 8:
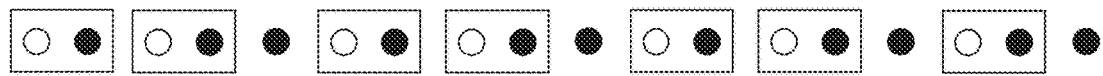

Specifically, the measurement information creation unit 13 monitors the displacement of the Y coordinate of the user's chest/waist area, and uses the frame at the time when the displacement changes from a negative value to a positive value as the ground contact timing. FIG. 6 is a diagram illustrating an example of changes over time in the value of the Y coordinate of the user's chest/waist area (y value) and a ground contact determination result. In FIG. 6, the solid line represents the ground contact determination. When the displacement of the Y coordinate of the chest/waist area changes from a negative value to a positive value, a value of "1" is obtained for the ground contact determination, and a state of ground contact is determined. In other cases, however, a value of "0" is obtained for the ground contact determination, and a state of no ground contact is determined. In FIG. 6, the broken line represents the y value of the chest/waist area.

Then, on the basis of the ground contact determination result, the measurement information creation unit 13 creates the measurement information indicated in FIG. 7, for example. FIG. 7 is a diagram illustrating an example of the measurement information created in the embodiment of the present invention. As indicated in FIG. 7, the measurement information records a pitch (sec) and a gait rhythm (sec) of the right leg and the left leg, for each amount of time elapsed from the start of image capturing.

In FIG. 7, the pitch represents the time between ground contact timings. In the case of the right foot, for example, the gait rhythm represents the time until the right foot next makes contact with the ground after the ground contact timing of the left foot. As such, by using the measurement information indicated in FIG. 7, the user's total number of steps can be calculated from the total number of changes in the value of the pitch. Identifying which of the left and right foot gait rhythm changes first makes it possible to identify the order of the ground contact feet as a ground contact history. Furthermore, the number of frames that have passed at the time of ground contact can be identified, as the ground contact history, from the number of frames until the gait rhythm changes.

In the present embodiment, the common part extraction unit 14 first identifies the total number of steps and the ground contact order from the measurement information in the first image data, and furthermore identifies the total number of steps and the ground contact order in the second image data. Then, from the skeletal information in both instances of image data, the common part extraction unit 14 extracts a common part of the ground contact history. For example, when a total number of steps of "5" and a ground contact history of "left, right, left, right, left" are identified from the measurement information in the first image data, and a total number of steps of "3" and a ground contact history of "right, left, right" are identified from the measurement information in the second image data, the common part extraction unit 14 identifies the "right, left, right" part in the two pieces of information as the common part. The common part extraction unit 14 then identifies the skeletal information corresponding to the part common between the first image data and the second image data, and extracts the identified skeletal information.

If the number of frames in the image data corresponding to the extracted skeletal information does not match between the first image data and the second image data, the correction processing unit 15 executes a process for aligning the number of frames. In other words, the correction processing unit 15 adds supplementary skeletal information to the skeletal information having the lower number of frames so that the number of frames in the extracted first image data and the number of frames in the extracted second image data match, and then corrects the skeletal information having the higher number of frames with the skeletal information having the lower number of frames.

The process for aligning the number of frames will be described using FIGS. 8(a) and (b). FIGS. 8(a) and (b) are diagrams illustrating an example of a supplementation process carried out in the embodiment of the present invention when the numbers of frames do not match. FIGS. 8(a) and (b) illustrate different examples.

In the example illustrated in FIG. 8(a), there are 10 frames in the first image data and 7 frames in the second image data, and it is therefore necessary to supplement the skeletal information in the second image data. The supplementing timing is determined by calculating a set number, a wait number, and a skip number, described next. Note that in the following descriptions, the skeletal information originally present is referred to as "actual data", and the supplementary skeletal information is referred to as "provisional data".

The set number is the number of pieces of provisional data constituting sets with the actual data, and is calculated by dividing the higher total frame number by the lower total frame number, discarding numbers below the decimal point in the obtained value, and subtracting 1 from the integer part. The wait number is the number of pieces of actual data that should appear before adding provisional data different from the provisional data added in accordance with the set number. The wait number is calculated by dividing the lower total frame number by the value of a remainder resulting from dividing the higher total frame number by the lower total frame number and then discarding numbers below the decimal point in the obtained value. The skip number is the number of times the wait number is skip counted, and is the value of the remainder obtained when calculating the wait number. "Skip counting" of the wait number refers to the number of times the first piece of actual data is excluded from the count when counting the number of pieces of actual data until the number of pieces of actual data reaches the wait number.

In the example in FIG. 8(a), the first image data has 10 frames and the second image data has 7 frames, and because 10 7=1.42 . . . (1 remainder 3), and 1−1=0, the set number is "0". Because 7±3=2.33 . . . (2 remainder 1), the wait number is of "2". The skip number is "1". As such, the post-supplement first image data and second image data are as indicated in FIG. 8(a). Specifically, in the example illustrated in FIG. 8(a), the set number is "0", and thus provisional data forming a set with the actual data is not added. Additionally, the skip number is "1" and the wait number is "2"; therefore, the first piece of actual data in the second image data is excluded from the wait number count, and provisional data is added after each of the third, fifth, and seventh piece of the actual data.

In the example illustrated in FIG. 8(b), the first image data has 18 frames and the second image data has 7 frames, and because 18±7=2.57 . . . (2 remainder 4), and 2−1=1, the set number is "1". Because 7±4=1.75 (1 remainder 3), of the wait number is "1". The skip number is "3". As such, the post-supplement first image data and second image data are as indicated in FIG. 8(b). In FIG. 8(b), each set of actual data and provisional data is enclosed in a square in order to indicate the sets. Specifically, in the example illustrated in FIG. 8(b), the set number is "1", and thus one piece of provisional data is added after each piece of actual data. The skip number is "3", and thus the wait number is skip-counted three times, such that the first, third, and fifth pieces of actual data in the second image data are excluded from the wait number count. Furthermore, the wait number is "1", and thus provisional data is added each time the wait number reaches 1; accordingly, provisional data is added before each of the third, fifth, and seventh pieces of actual data.

In FIGS. 8(a) and (b), the black dots indicate supplemented skeletal information. The actual data of the previous frame is used for the supplemented skeletal information. In other words, skeletal information indicated by a black dot is the same as skeletal information to the left thereof, indicated by a white dot.

After the process for aligning the numbers of frames, the correction processing unit 15 identifies the travel direction of the user from when the first image data was obtained and the travel direction of the user from when the second image data was obtained, in order to correct the skeletal information having a higher number of frames with the skeletal information having a lower number of frames.

Figure 9:
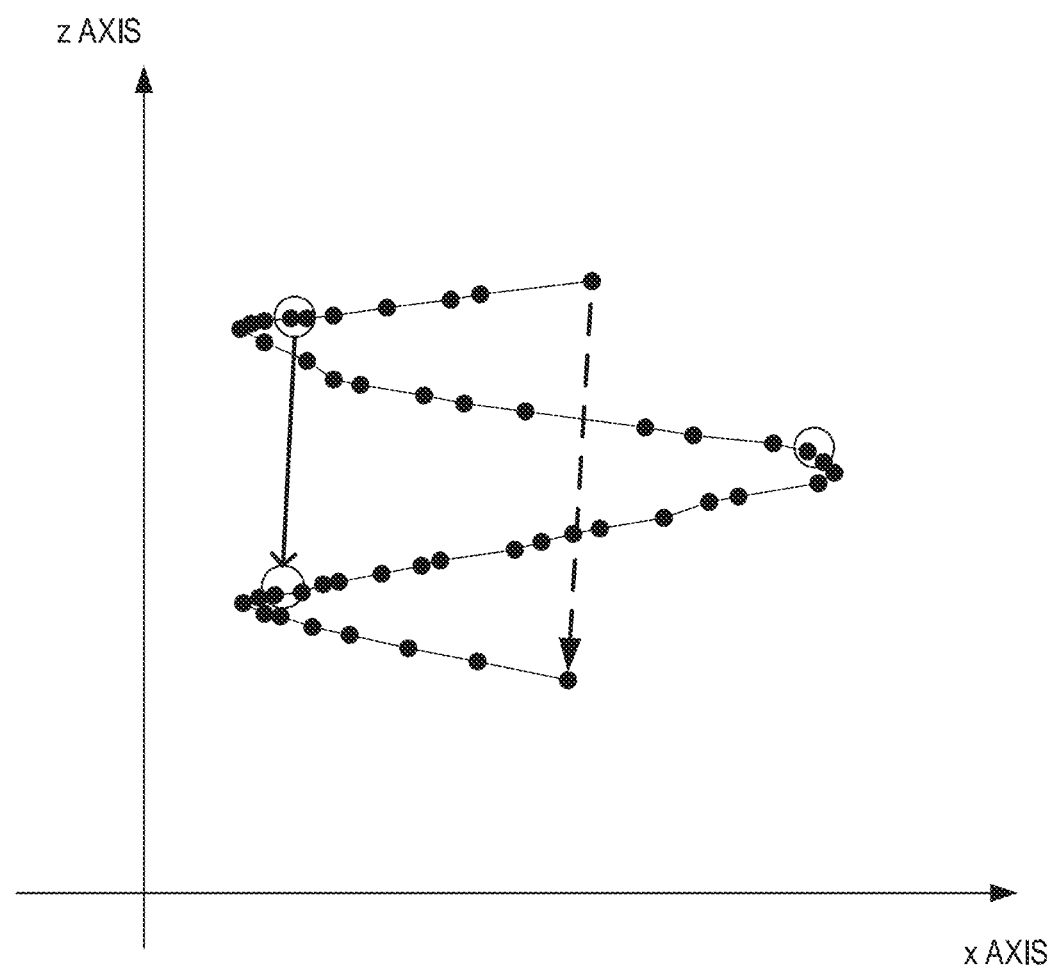
FIG. 9 is a diagram illustrating an example of changes over time in the value of an x coordinate (an x value) and a z coordinate (z value) of the user's chest/waist area.
Figure 10:
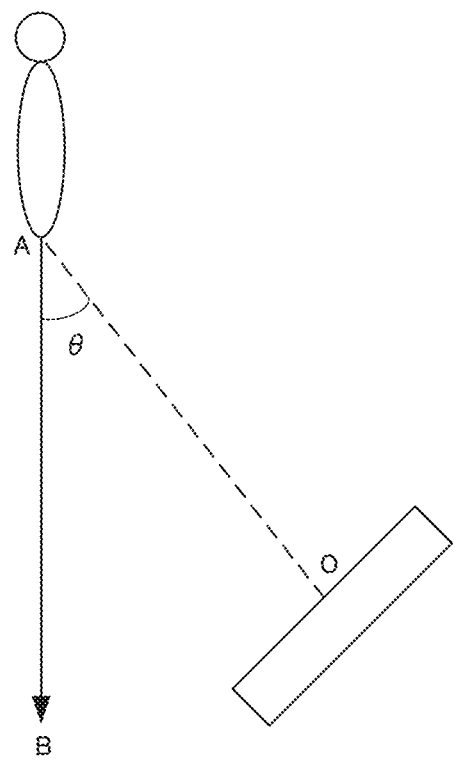
FIG. 10 is a diagram illustrating an example of a relationship between a user's travel direction and a position of a depth sensor.

In the present embodiment, the correction processing unit 15 calculates a motion vector of the chest/waist area in the horizontal plane (a plane including the X axis and the Z axis) from changes in the three-dimensional coordinates of the chest/waist area, and then uses the calculated motion vector to calculate an angle θ of the travel direction of the user relative to the image capturing plane of the depth sensor. FIG. 9 is a diagram illustrating an example of changes over time in the value of the x coordinate (the x value) and the z coordinate (the z value) of the user's chest/waist area. FIG. 10 is a diagram illustrating an example of a relationship between the user's travel direction and the position of the depth sensor.

In FIG. 9, the solid line graph obtained from the plotted black circles represents the x values and the z values of the chest/waist area, and the parts enclosed in circles indicate the ground contact timings. In particular, the circle located on the left side of the graph indicates the ground contact timing of the user's right foot, and the circle located on the right side indicates the ground contact timing of the user's left foot. In FIG. 10, the arrow AB corresponds to a motion vector AB indicating the user's travel direction. O represents a given point in the image capturing plane of the depth sensor.

Specifically, as illustrated in FIG. 9, the correction processing unit 15 identifies the ground contact timing of one of the user's feet from the change over time in the x value and the z value of the chest/waist area, obtains a vector by connecting the identified ground contact points, and identifies the user's travel direction by taking the vector that has been obtained as the motion vector AB. The correction processing unit 15 may also specify a start point and an end point of data acquisition, obtain a vector by connecting the identified start point and end point, and identify the user's travel direction by taking the vector that has been obtained as the motion vector AB.

In FIG. 9, the solid line arrow represents the motion vector found from the ground contact timing, and the broken line arrow represents the motion vector found from the start point and the end point of the data acquisition.

After identifying the user's motion vector AB through either of the aforementioned methods, the correction processing unit 15 furthermore obtains a vector AO from the position of the depth sensor and the position of the user at the start of data acquisition, and then calculates the angle θ using the following Equation 4.

$$\cos\theta = \frac{\overrightarrow{AB} \cdot \overrightarrow{AO}}{|\overrightarrow{AB}||\overrightarrow{AO}|} \quad \text{[Equation 4]}$$

Additionally, after identifying the user's travel direction both from when the first image data was acquired and when the second image data was acquired, the correction processing unit 15 converts the three-dimensional coordinates of each joint in one or both pieces of skeletal information so that the identified travel directions match, by rotating the coordinates central to the y axis using the angle θ of the user's identified travel direction.

Figure 11A:
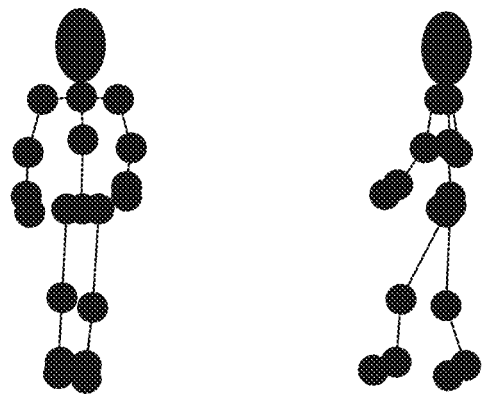
FIGS. 11(a)-11(c) are diagrams illustrating corrections made to skeletal information according to the embodiment of the present invention, where
Figure 11B:
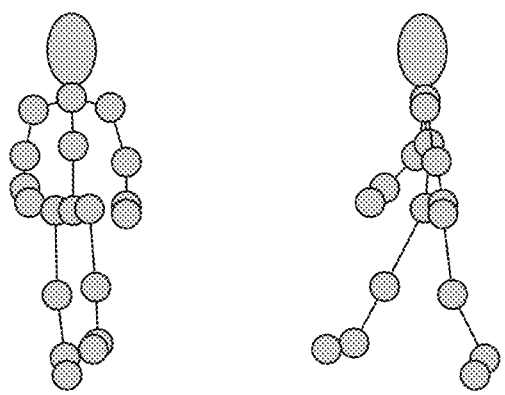
Figure 11C:
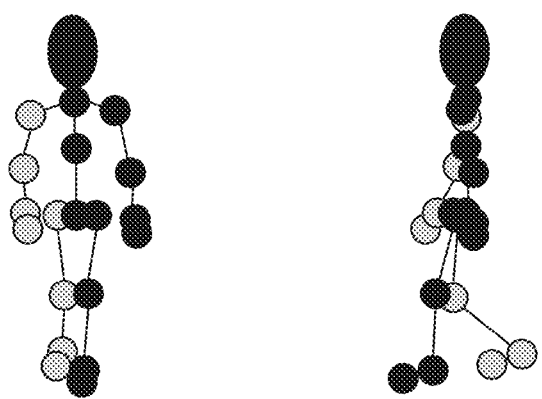

Then, the correction processing unit 15 combines the skeletal information in the first image data with the skeletal information in the second image data through correction to create new skeletal information. This point will be described using FIGS. 11(a)-11(c). FIGS. 11(a)-11(c) are diagrams illustrating corrections made to the skeletal information according to the embodiment of the present invention, where FIG. 11(a) illustrates an example of the skeletal information in the first image data, FIG. 11(b) illustrates an example of the skeletal information in the second image data, and FIG. 11(c) illustrates an example of the skeletal information after correction.

The skeletal information is actually constituted by three-dimensional information of each joint, as illustrated in FIG. 4, both before and after the correction. However, in the examples illustrated in FIGS. 11(a) to (c), the skeletal information is depicted as a skeleton for the sake of simplicity. Additionally, only the main joints are illustrated in FIGS. 11(a) to (c), rather than all of the joints included in the skeletal information. Furthermore, in FIGS. 11(a) to (c), the skeleton on the left side corresponds to a skeleton from when the user is captured from the front, and the skeleton on the right corresponds to a skeleton from when the user is captured from the right side.

For example, assume that the first direction is a direction angled to the right relative to the user's travel direction, the second direction is a direction angled to the left relative to the walking user's travel direction, and the second image data has a higher number of frames than the first image data. In this case, as illustrated in FIG. 11(c), the correction processing unit 15 replaces the positions of the joints in the arm and leg on the right side in the skeletal information of the second image data with the positions of the joints in the arm and leg on the right side in the skeletal information of the first image data.

Note that if the first image data has a higher number of frames than the second image data, the correction processing unit 15 replaces the positions of the joints in the arm and leg on the left side in the skeletal information of the first image data with the positions of the joints in the arm and leg on the left side in the skeletal information of the second image data.

In the present embodiment, the analysis processing unit 16 uses the corrected skeletal information to calculate gait information indicating knee extension, toe tip lift, and so on, and displays the calculated gait information in a display screen. The analysis processing unit 16 can also display the skeletons obtained from the skeletal information (see FIGS. 11(a) to (c)) in the display screen.

[Device Operations]

Figure 12:
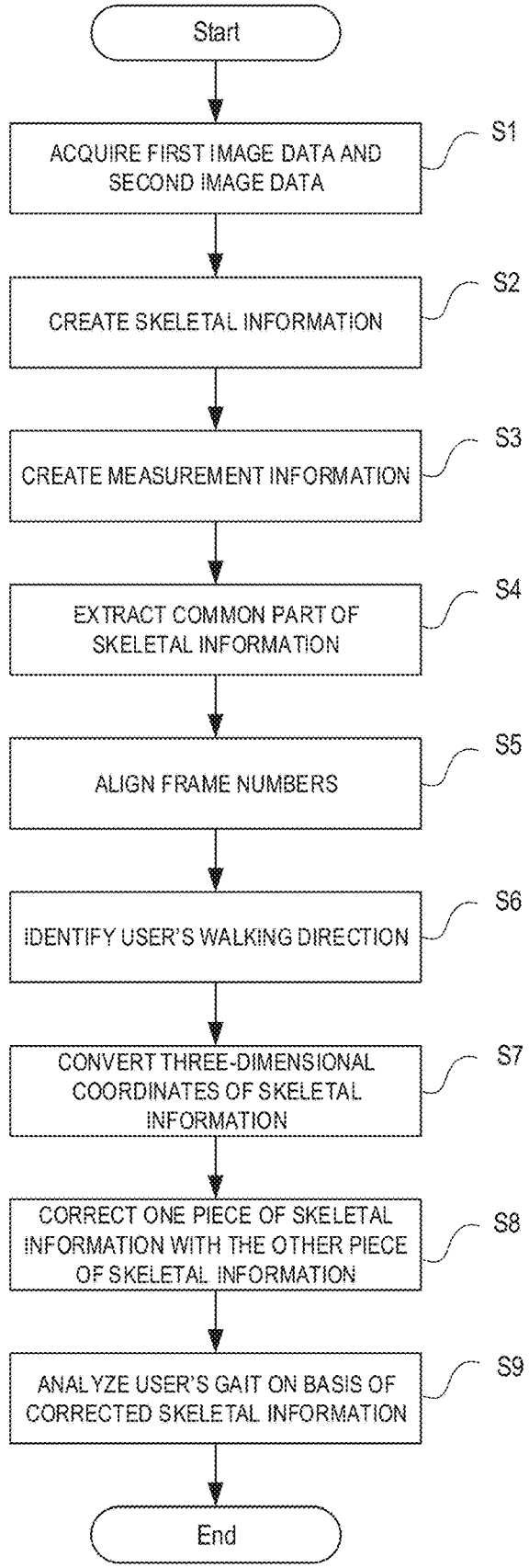
FIG. 12 is a flowchart illustrating operations of the gait analyzing device according to the embodiment of the present invention.

Next, operations of the gait analyzing device 10 according to the embodiment of the present invention will be described using FIG. 12. FIG. 12 is a flowchart illustrating operations of the gait analyzing device 10 according to the embodiment of the present invention. The following descriptions will refer to FIGS. 1 to 11 as appropriate. In the present embodiment, the gait analyzing method is realized by causing the gait analyzing device 10 to operate. As such, the following descriptions of the operations of the gait analyzing device 10 will be given in place of descriptions of the gait analyzing method according to the present embodiment.

As illustrated in FIG. 12, first, the data acquisition unit 11 acquires the first image data from the depth sensor 20 and acquires the second image data from the depth sensor 21 (step S1). The data acquisition unit 11 passes the acquired image data to the skeletal information creation unit 12.

Next, the skeletal information creation unit 12 calculates the three-dimensional coordinates of specific joints of the user for each piece of image data, by using coordinates in the image data and the depths added to the pixels, and creates the skeletal information using the calculated three-dimensional coordinates (step S2). The skeletal information creation unit 12 passes the created skeletal information to the common part extraction unit 14.

Next, the measurement information creation unit 13 identifies the ground contact timing for each of the first image data and the second image data, and creates the measurement information from the identified ground contact timings (step S3). The measurement information creation unit 13 passes the created measurement information to the common part extraction unit 14.

Next, the common part extraction unit 14 identifies the total number of steps and the ground contact order from the measurement information in the first image data, identifies the total number of steps and the ground contact order in the second image data, and then, from the skeletal information in both instances of image data, identifies a common part of the ground contact history (step S4).

Next, if the number of frames in the image data corresponding to the extracted skeletal information does not match between the first image data and the second image data, the correction processing unit 15 executes a process for aligning the number of frames (step S5). Note that step S5 is skipped if the number of frames in the image data corresponding to the extracted skeletal information matches between the first image data and the second image data.

Next, the correction processing unit 15 identifies the user's travel direction from when the first image data was acquired and the user's travel direction from when the second image data was acquired (step S6). Then, after identifying the user's travel direction from when the image data was acquired, the correction processing unit 15 converts the three-dimensional coordinates of each joint in one or both pieces of skeletal information so that the identified travel directions match, by rotating the coordinates central to the y axis using the angle θ of the user's identified travel direction (step S7).

Next, the correction processing unit 15 combines the skeletal information in the first image data with the skeletal information in the second image data through correction to create new skeletal information (step S8). The correction processing unit 15 passes the corrected new skeletal information to the analysis processing unit 16.

Next, the analysis processing unit 16 analyzes the user's gait using the corrected skeletal information (step S9). Specifically, the analysis processing unit 16 uses the corrected skeletal information to calculate gait information indicating knee extension, toe tip lift, and so on, and displays the calculated gait information in a display screen. The analysis processing unit 16 also displays the skeletons obtained from the skeletal information (see FIG. 11(c)) in the display screen.

As described thus far, according to the present embodiment, the same skeletal information as when capturing an image of a walking user from the front can be obtained when capturing an image of the user from an angle. This suppresses a situation in which the user inadvertently mistakes the depth sensor for an obstacle and suddenly reduces his/her walking speed or changes his/her path near the depth sensor when images are being captured, which achieves an improvement in the accuracy of the gait analysis.

[Program]

A program according to the present embodiment may be any program that causes a computer to execute steps S1 to S9 illustrated in FIG. 12. The gait analyzing device 10 and the gait analyzing method according to the present embodiment can be realized by installing the program in a computer and executing the program. In this case, a CPU (Central Processing Unit) of the computer carries out processing by functioning as the data acquisition unit 11, the skeletal information creation unit 12, the measurement information creation unit 13, the common part extraction unit 14, the correction processing unit 15, and the analysis processing unit 16.

The program according to the present embodiment may be executed by a computer system constructed from a plurality of computers. In this case, for example, each computer may function as any of the data acquisition unit 11, the skeletal information creation unit 12, the measurement information creation unit 13, the common part extraction unit 14, the correction processing unit 15, and the analysis processing unit 16.

[Physical Configuration]

Figure 13:
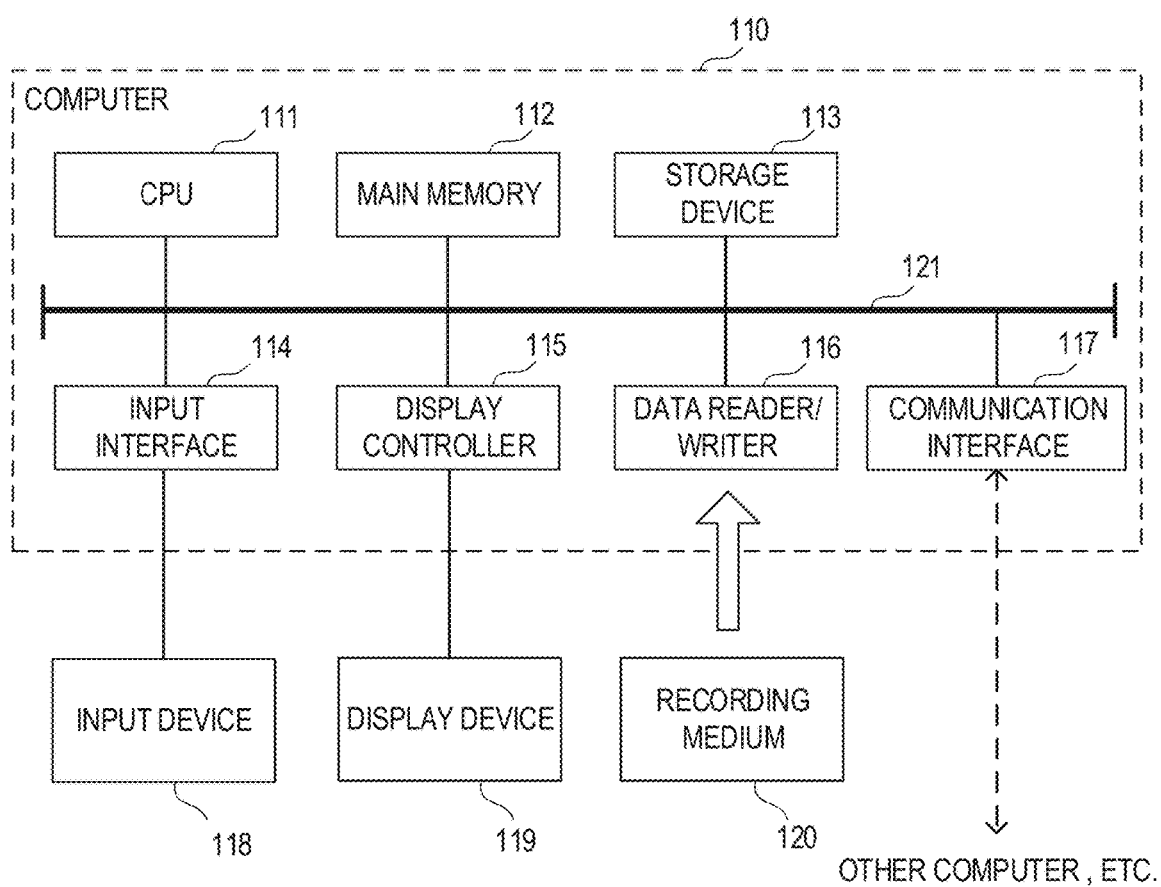
FIG. 13 is a block diagram illustrating an example of a computer realizing the gait analyzing device according to the embodiment of the present invention.

A computer that realizes the gait analyzing device 10 by executing the program according to the present embodiment will be described using FIG. 13. FIG. 13 is a block diagram illustrating an example of a computer realizing the gait analyzing device 10 according to the embodiment of the present invention.

As illustrated in FIG. 13, a computer 110 includes a CPU 111, main memory 112, a storage device 113, an input interface 114, a display controller 115, a data reader/writer 116, and a communication interface 117. These units are connected by a bus 121 so as to be capable of data communication with each other.

The CPU 111 loads the program (code) according to the present embodiment, which is stored in the storage device 113, into the main memory 112, and executes the program according to a prescribed sequence, thereby carrying out various types of operations. The main memory 112 is typically a volatile storage device such as DRAM (Dynamic Random Access Memory) or the like. The program according to the present embodiment is stored in a computer-readable recording medium 120 and provided in such a state. Note that the program according to the present embodiment may be distributed over the Internet, which is connected via the communication interface 117.

In addition to a hard disk drive, a semiconductor storage device such as flash memory or the like can be given as a specific example of the storage device 113. The input interface 114 facilitates data transfer between the CPU 111 and an input device 118 such as a keyboard and a mouse. The display controller 115 can be connected to a display device 119, and controls displays made in the display device 119.

The data reader/writer 116 facilitates data transfer between the CPU 111 and the recording medium 120, reads out programs from the recording medium 120, and writes results of processing performed by the computer 110 into the recording medium 120. The communication interface 117 facilitates data exchange between the CPU 111 and other computers.

A generic semiconductor storage device such as CF (Compact Flash (registered trademark)), SD (Secure Digital), or the like, a magnetic storage medium such as a flexible disk or the like, an optical storage medium such as a CD-ROM (Compact Disk Read Only Memory) or the like, and so on can be given as specific examples of the recording medium 120.

Note that the gait analyzing device 10 according to the present embodiment can also be realized using hardware corresponding to the respective units, instead of a computer in which a program is installed. Furthermore, the gait analyzing device 10 may be partially realized by a program, with the remaining parts realized by hardware.

All or part of the above-described embodiment can be expressed as Addendum 1 to Addendum 9, described hereinafter, but is not intended to be limited to the following descriptions.

(Addendum 1)

A gait analyzing device comprising:

a data acquisition unit that acquires, on a frame-by-frame basis, first image data obtained by using a depth sensor to capture an image of a walking user from a first direction angled relative to a travel direction and second image data obtained by using the depth sensor or a different depth sensor to capture an image of the walking user from a second direction angled, at a different direction from the first direction, relative to the travel direction;

a skeletal information creation unit that creates skeletal information identifying the position of a specific joint of the user, for all of the acquired image data, using depth information included in each of the first image data and the second image data;

a measurement information creation unit that creates measurement information identifying a total number of steps by the user and a ground contact history of the user's left and right feet, using all of the acquired image data, for each of the first image data and the second image data;

a common part extraction unit that compares the measurement information in all of the acquired first image data with the measurement information in all of the acquired second image data, and extracts, from the skeletal information in all of the acquired first image data and the skeletal information in all of the acquired second image data, a part where the ground contact history of the user's left and right feet is common;

a correction processing unit that, of the skeletal information in the extracted first image data and the skeletal information in the extracted second image data, corrects the skeletal information of the image data having the higher number of frames using the skeletal information of the image data having the lower number of frames; and an analysis processing unit that analyzes the user's gait using the corrected skeletal information.

(Addendum 2)

The gait analyzing device according to Addendum 1, wherein the correction processing unit adds supplementary skeletal information to the skeletal information having the lower number of frames so that the number of frames in the extracted first image data and the number of frames in the extracted second image data match, and then corrects the skeletal information having the higher number of frames with the skeletal information having the lower number of frames.

(Addendum 3)

The gait analyzing device according to Addendum 1 or 2, wherein the first direction is a direction angled to the right relative to the travel direction of the walking user, and the second direction is a direction angled to the left relative to the travel direction of the walking user; and the correction processing unit:

replaces the positions of the joints in an arm and a leg on the left side in the skeletal information of the first image data with the positions of the joints in the arm and the leg on the left side in the skeletal information of the second image data when the number of frames in the first image data is higher than the number of frames in the second image data; and replaces the positions of the joints in an arm and a leg on the right side in the skeletal information of the second image data with the positions of the joints in the arm and the leg on the right side in the skeletal information of the first image data when the number of frames in the second image data is higher than the number of frames in the first image data.

(Addendum 4)

A gait analyzing method comprising:

(a) a step of acquiring, on a frame-by-frame basis, first image data obtained by using a depth sensor to capture an image of a walking user from a first direction angled relative to a travel direction and second image data obtained by using the depth sensor or a different depth sensor to capture an image of the walking user from a second direction angled, at a different direction from the first direction, relative to the travel direction;

(b) a step of creating skeletal information identifying the position of a specific joint of the user, for all of the acquired image data, using depth information included in each of the first image data and the second image data;

(c) a step of creating measurement information identifying a total number of steps by the user and a ground contact history of the user's left and right feet, using all of the acquired image data, for each of the first image data and the second image data;

(d) a step of comparing the measurement information in all of the acquired first image data with the measurement information in all of the acquired second image data, and extracting, from the skeletal information in all of the acquired first image data and the skeletal information in all of the acquired second image data, a part where the ground contact history of the user's left and right feet is common;

(e) a step of correcting, of the skeletal information in the extracted first image data and the skeletal information in the extracted second image data, the skeletal information of the image data having the higher number of frames using the skeletal information of the image data having the lower number of frames; and (f) a step of analyzing the user's gait using the corrected skeletal information.

(Addendum 5)

The gait analyzing method according to Addendum 4, wherein in step (e), supplementary skeletal information is added to the skeletal information having the lower number of frames so that the number of frames in the extracted first image data and the number of frames in the extracted second image data match, and then the skeletal information having the higher number of frames is corrected with the skeletal information having the lower number of frames.

(Addendum 6)

The gait analyzing method according to Addendum 4 or 5, wherein the first direction is a direction angled to the right relative to the travel direction of the walking user, and the second direction is a direction angled to the left relative to the travel direction of the walking user; and in step (e):

the positions of the joints in an arm and a leg on the left side in the skeletal information of the first image data are replaced with the positions of the joints in the arm and the leg on the left side in the skeletal information of the second image data when the number of frames in the first image data is higher than the number of frames in the second image data; and the positions of the joints in an arm and a leg on the right side in the skeletal information of the second image data are replaced with the positions of the joints in the arm and the leg on the right side in the skeletal information of the first image data when the number of frames in the second image data is higher than the number of frames in the first image data.

(Addendum 7)

A computer-readable recording medium storing a program including commands causing a computer to execute:

(a) a step of acquiring, on a frame-by-frame basis, first image data obtained by using a depth sensor to capture an image of a walking user from a first direction angled relative to a travel direction and second image data obtained by using the depth sensor or a different depth sensor to capture an image of the walking user from a second direction angled, at a different direction from the first direction, relative to the travel direction;

(b) a step of creating skeletal information identifying the position of a specific joint of the user, for all of the acquired image data, using depth information included in each of the first image data and the second image data;

(c) a step of creating measurement information identifying a total number of steps by the user and a ground contact history of the user's left and right feet, using all of the acquired image data, for each of the first image data and the second image data;

(d) a step of comparing the measurement information in all of the acquired first image data with the measurement information in all of the acquired second image data, and extracting, from the skeletal information in all of the acquired first image data and the skeletal information in all of the acquired second image data, a part where the ground contact history of the user's left and right feet is common;

(e) a step of correcting, of the skeletal information in the extracted first image data and the skeletal information in the extracted second image data, the skeletal information of the image data having the higher number of frames using the skeletal information of the image data having the lower number of frames; and (f) a step of analyzing the user's gait using the corrected skeletal information.

(Addendum 8)

The computer-readable recording medium according to Addendum 7, wherein in step (e), supplementary skeletal information is added to the skeletal information having the lower number of frames so that the number of frames in the extracted first image data and the number of frames in the extracted second image data match, and then the skeletal information having the higher number of frames is corrected with the skeletal information having the lower number of frames.

(Addendum 9)

The computer-readable recording medium according to Addendum 7 or 8, wherein the first direction is a direction angled to the right relative to the travel direction of the walking user, and the second direction is a direction angled to the left relative to the travel direction of the walking user; and in step (e):

the positions of the joints in an arm and a leg on the left side in the skeletal information of the first image data are replaced with the positions of the joints in the arm and the leg on the left side in the skeletal information of the second image data when the number of frames in the first image data is higher than the number of frames in the second image data; and the positions of the joints in an arm and a leg on the right side in the skeletal information of the second image data are replaced with the positions of the joints in the arm and the leg on the right side in the skeletal information of the first image data when the number of frames in the second image data is higher than the number of frames in the first image data.

While the present invention has been described above with reference to embodiments, the present invention is not intended to be limited to the above embodiments. Many variations can be made, by one of ordinary skill in the art, on the configuration and details of the present invention without departing from the scope of the present invention.

INDUSTRIAL APPLICABILITY

According to the present invention, the accuracy of analysis can be improved when analyzing walking motion using a depth sensor. The present invention is therefore useful in various fields in which it is necessary to analyze a person's gait.

DESCRIPTION OF REFERENCE NUMERALS

10 Gait Analyzing Device
11 Data Acquisition Unit
12 Skeletal Information Creation Unit
13 Measurement Information Creation Unit
14 Common Part Extraction Unit
15 Correction Processing Unit
16 Analysis Processing Unit
20, 21 Depth Sensor
30 User
110 Computer
111 CPU
112 Main Memory
113 Storage Device
114 Input Interface
115 Display Controller
116 Data Reader/Writer
117 Communication Interface
118 Input Device
119 Display Device
120 Recording Medium
121 Bus

The invention claimed is:

1. A gait analyzing device comprising:
one or more processors; and
a memory storing an executable program that, when executed by the one or more processors, causes the one or more processors to:
acquire, on a frame-by-frame basis, first image data obtained by using a depth sensor to capture an image of a walking user from a first direction angled relative to a travel direction and second image data obtained by using the depth sensor or a different depth sensor to capture an image of the walking user from a second direction angled, at a different direction from the first direction, relative to the travel direction;
create skeletal information identifying the position of a specific joint of the user, for all of the acquired image data, using depth information included in each of the first image data and the second image data;
create measurement information identifying a total number of steps by the user and a ground contact history of the user's left and right feet, using all of the acquired image data, for each of the first image data and the second image data;
compare the measurement information in all of the acquired first image data with the measurement information in all of the acquired second image data, and extract, from the skeletal information in all of the acquired first image data and the skeletal information in all of the acquired second image data, a part where the ground contact history of the user's left and right feet is common;
of the skeletal information in the extracted first image data and the skeletal information in the extracted second image data, correct the skeletal information of the image data having the higher number of frames using the skeletal information of the image data having the lower number of frames; and
analyze the user's gait using the corrected skeletal information.

2. The gait analyzing device according to claim 1, wherein the one or more processors further:
add supplementary skeletal information to the skeletal information having the lower number of frames so that the number of frames in the extracted first image data and the number of frames in the extracted second image data match, and then corrects the skeletal information having the higher number of frames with the skeletal information having the lower number of frames.

3. The gait analyzing device according to claim 1, wherein the first direction is a direction angled to the right relative to the travel direction of the walking user, and the second direction is a direction angled to the left relative to the travel direction of the walking user; and
wherein the one or more processors further:
replace the positions of the joints in an arm and a leg on the left side in the skeletal information of the first image data with the positions of the joints in the arm and the leg on the left side in the skeletal information of the second image data when the number of frames in the first image data is higher than the number of frames in the second image data; and
replace the positions of the joints in an arm and a leg on the right side in the skeletal information of the second image data with the positions of the joints in the arm and the leg on the right side in the skeletal information of the first image data when the number of frames in the second image data is higher than the number of frames in the first image data.

4. A gait analyzing method comprising:
(a) acquiring, on a frame-by-frame basis, first image data obtained by using a depth sensor to capture an image of a walking user from a first direction angled relative to a travel direction and second image data obtained by using the depth sensor or a different depth sensor to capture an image of the walking user from a second direction angled, at a different direction from the first direction, relative to the travel direction;
(b) creating skeletal information identifying the position of a specific joint of the user, for all of the acquired image data, using depth information included in each of the first image data and the second image data;
(c) creating measurement information identifying a total number of steps by the user and a ground contact history of the user's left and right feet, using all of the acquired image data, for each of the first image data and the second image data;
(d) comparing the measurement information in all of the acquired first image data with the measurement information in all of the acquired second image data, and extracting, from the skeletal information in all of the acquired first image data and the skeletal information in all of the acquired second image data, a part where the ground contact history of the user's left and right feet is common;
(e) correcting, of the skeletal information in the extracted first image data and the skeletal information in the extracted second image data, the skeletal information of the image data having the higher number of frames using the skeletal information of the image data having the lower number of frames; and
(f) analyzing the user's gait using the corrected skeletal information.

5. The gait analyzing method according to claim 4, wherein in (e), supplementary skeletal information is added to the skeletal information having the lower number of frames so that the number of frames in the extracted first image data and the number of frames in the extracted second image data match, and then the skeletal information having the higher number of frames is corrected with the skeletal information having the lower number of frames.

6. The gait analyzing method according to claim 4,
wherein the first direction is a direction angled to the right relative to the travel direction of the walking user, and the second direction is a direction angled to the left relative to the travel direction of the walking user; and
in (e):
the positions of the joints in an arm and a leg on the left side in the skeletal information of the first image data are replaced with the positions of the joints in the arm and the leg on the left side in the skeletal information of the second image data when the number of frames in the first image data is higher than the number of frames in the second image data; and
the positions of the joints in an arm and a leg on the right side in the skeletal information of the second image data are replaced with the positions of the joints in the arm and the leg on the right side in the skeletal information of the first image data when the number of frames in the second image data is higher than the number of frames in the first image data.

7. A non-transitory computer-readable recording medium storing a program including commands causing a computer to execute:
(a) acquire, on a frame-by-frame basis, first image data obtained by using a depth sensor to capture an image of a walking user from a first direction angled relative to a travel direction and second image data obtained by using the depth sensor or a different depth sensor to capture an image of the walking user from a second direction angled, at a different direction from the first direction, relative to the travel direction;
(b) create skeletal information identifying the position of a specific joint of the user, for all of the acquired image data, using depth information included in each of the first image data and the second image data;
(c) create measurement information identifying a total number of steps by the user and a ground contact history of the user's left and right feet, using all of the acquired image data, for each of the first image data and the second image data;
(d) compare the measurement information in all of the acquired first image data with the measurement information in all of the acquired second image data, and extracting, from the skeletal information in all of the acquired first image data and the skeletal information in all of the acquired second image data, a part where the ground contact history of the user's left and right feet is common;
(e) correct, of the skeletal information in the extracted first image data and the skeletal information in the extracted second image data, the skeletal information of the image data having the higher number of frames using the skeletal information of the image data having the lower number of frames; and
(f) analyze the user's gait using the corrected skeletal information.

8. The non-transitory computer-readable recording medium according to claim 7,
wherein in (e), supplementary skeletal information is added to the skeletal information having the lower number of frames so that the number of frames in the extracted first image data and the number of frames in the extracted second image data match, and then the skeletal information having the higher number of frames is corrected with the skeletal information having the lower number of frames.

9. The non-transitory computer-readable recording medium according to claim 7,
wherein the first direction is a direction angled to the right relative to the travel direction of the walking user, and the second direction is a direction angled to the left relative to the travel direction of the walking user; and
in (e):
the positions of the joints in an arm and a leg on the left side in the skeletal information of the first image data are replaced with the positions of the joints in the arm and the leg on the left side in the skeletal information of the second image data when the number of frames in the first image data is higher than the number of frames in the second image data; and
the positions of the joints in an arm and a leg on the right side in the skeletal information of the second image data are replaced with the positions of the joints in the arm and the leg on the right side in the skeletal information of the first image data when the number of frames in the second image data is higher than the number of frames in the first image data.

\* \* \* \* \*